United States Patent
Tupin, Jr.

(10) Patent No.: US 12,268,518 B2
(45) Date of Patent: *Apr. 8, 2025

(54) MEDICAL RADAR SYSTEM FOR GUIDING CARDIAC RESUSCITATION

(71) Applicant: Lifewave Biomedical, Inc., Los Altos, CA (US)

(72) Inventor: Joe Paul Tupin, Jr., Los Altos, CA (US)

(73) Assignee: Lifewave Biomedical, Inc., Los Altos, CA (US)

( * ) Notice: Subject to any disclaimer, the term of this patent is extended or adjusted under 35 U.S.C. 154(b) by 840 days.

This patent is subject to a terminal disclaimer.

(21) Appl. No.: 17/351,673

(22) Filed: Jun. 18, 2021

(65) Prior Publication Data

US 2021/0307685 A1 Oct. 7, 2021

Related U.S. Application Data

(63) Continuation of application No. 15/354,905, filed on Nov. 17, 2016, now Pat. No. 11,039,785, which is a
(Continued)

(51) Int. Cl.
*A61B 5/02* (2006.01)
*A61B 5/00* (2006.01)
(Continued)

(52) U.S. Cl.
CPC .......... *A61B 5/4848* (2013.01); *A61B 5/0205* (2013.01); *A61B 5/021* (2013.01);
(Continued)

(58) Field of Classification Search
None
See application file for complete search history.

(56) References Cited

U.S. PATENT DOCUMENTS

| | | |
|---|---|---|
| 3,483,860 A | 12/1969 | Stanley |
| 4,926,868 A | 5/1990 | Larsen |

(Continued)

FOREIGN PATENT DOCUMENTS

| | | |
|---|---|---|
| CN | 1819855 | 8/2006 |
| GB | 201113907.8 | 2/2013 |

(Continued)

OTHER PUBLICATIONS

Dissanayake et al., UWB Antenna Impedance Matching in Biomedical Implants, Antenna and Propagation, EUCAP 2009, pp. 3523-3526.

(Continued)

*Primary Examiner* — Patricia J Park
(74) *Attorney, Agent, or Firm* — Haverstock & Owens, A Law Corporation

(57) ABSTRACT

Medical radar devices, including ultra-wideband (UWB) devices, for use in assisting and/or guiding cardiopulmonary resuscitation (CPR) by indicating one or more of: compression depth, compression frequency, and a return to spontaneous circulation. The devices and methods described herein may use reflected energy applied to a patient's chest to determine cardiac motion and/or chest compression and provide feedback to the person applying the CPR. In some variations the device is incorporated as a part of another resuscitation device, such as a defibrillator or automatic compression device.

28 Claims, 8 Drawing Sheets

Related U.S. Application Data continuation of application No. 14/404,386, filed as application No. PCT/US2013/043337 on May 30, 2013, now abandoned.

(60) Provisional application No. 61/653,724, filed on May 31, 2012.

(51) Int. Cl.

| | | |
|---|---|---|
| *A61B 5/0205* | (2006.01) | |
| *A61B 5/021* | (2006.01) | |
| *A61B 5/024* | (2006.01) | |
| *A61B 5/0507* | (2021.01) | |
| *A61B 5/11* | (2006.01) | |
| *A61H 31/00* | (2006.01) | |
| *A61N 1/39* | (2006.01) | |

(52) U.S. Cl.
CPC ............ *A61B 5/024* (2013.01); *A61B 5/0507* (2013.01); *A61B 5/11* (2013.01); *A61B 5/7405* (2013.01); *A61B 5/742* (2013.01); *A61B 5/7455* (2013.01); *A61H 31/005* (2013.01); *A61H 31/007* (2013.01); *A61N 1/3925* (2013.01); *A61B 5/6823* (2013.01); *A61B 2505/01* (2013.01); *A61H 2201/5015* (2013.01); *A61H 2201/5058* (2013.01); *A61H 2201/5097* (2013.01); *A61H 2203/0456* (2013.01); *A61H 2205/084* (2013.01); *A61H 2230/30* (2013.01)

(56) References Cited

U.S. PATENT DOCUMENTS

| | | | |
|---|---|---|---|
| 5,172,690 | A | 12/1992 | Nappholz et al. |
| 5,315,995 | A | 5/1994 | Rivers |
| 5,573,012 | A | 11/1996 | McEwan |
| 5,841,288 | A | 11/1998 | Meaney |
| 5,853,005 | A | 12/1998 | Scanlon |
| 5,986,600 | A | 11/1999 | McEwan |
| 6,473,640 | B1 | 10/2002 | Erlebacher |
| 8,068,051 | B1 | 11/2011 | Osterwil |
| 8,721,559 | B2 | 5/2014 | Peterson |
| 9,002,427 | B2 | 4/2015 | Tupin, Jr. |
| 2002/0140215 | A1 | 10/2002 | Breed |
| 2002/0156379 | A1 | 10/2002 | Angelsen |
| 2003/0083714 | A1 | 5/2003 | Thompson |
| 2004/0249257 | A1 | 12/2004 | Tupin, Jr. |
| 2004/0249258 | A1 | 12/2004 | Tupin, Jr. |
| 2005/0052322 | A1 | 3/2005 | Park |
| 2005/0128124 | A1 | 6/2005 | Greneker, III |
| 2006/0058681 | A1 | 3/2006 | Eberle |
| 2006/0111642 | A1 | 5/2006 | Baura |
| 2006/0287600 | A1* | 12/2006 | McEowen .......... A61B 5/14535 600/481 |
| 2007/0057843 | A1 | 3/2007 | Chang |
| 2007/0179397 | A1 | 8/2007 | Hashimshony |
| 2007/0197891 | A1 | 8/2007 | Shachar |
| 2008/0001735 | A1 | 1/2008 | Tran |
| 2008/0015439 | A1 | 1/2008 | Raju et al. |
| 2008/0252293 | A1 | 10/2008 | Lagae |
| 2008/0294019 | A1 | 11/2008 | Tran |
| 2009/0054737 | A1 | 2/2009 | Magar |
| 2009/0227882 | A1 | 9/2009 | Foo |
| 2009/0238426 | A1 | 9/2009 | Fear |
| 2010/0152600 | A1 | 6/2010 | Droitcour et al. |
| 2011/0112423 | A1* | 5/2011 | Chapman ................. A61B 5/02 600/528 |
| 2016/0361041 | A1 | 12/2016 | Barsimantov |

FOREIGN PATENT DOCUMENTS

| | | |
|---|---|---|
| JP | 3156725 | 4/2001 |
| WO | 2008148040 A1 | 12/2008 |
| WO | 2009031149 A2 | 3/2009 |
| WO | 2009031150 A2 | 3/2009 |

OTHER PUBLICATIONS

Staderini, UWB Radars in Medicine, Jan. 2002, IEEE AESS Systems Magazine, pp. 13-18.

James C. Lin, "Microwave Sensing of Physiological Movement and Volume Change": A review, University of Illinois, 1992, pp. 557-565.

Staderini, "UWV Radars in Medicine.," IEEE Aerospace and Electronic Systems Magazine, 2002.

Droitcour, Non-contract measurement of Heart and Respiration Rates with a Single-Chip Microwave Doppler Radar, Stanford University 2006.

Boryssenko, Anatoliy,. & Boryssenko, Elen, UWB Radar Sensor to Monitor Heart Physiology, 10.1109/LAPC.2011.6114039, 2011.

Salvatore Caorsi et al., Numerical Assessment Concerning a Focused Microwave Diagnostic Method for Medical Applications, 2000 IEEE Trans. Microwave Theory and Techniques 48:1815-1830 (Year 2000).

Guido Biffi Gentili et al. "A Versatile Microwave Plethysmograph for the Monitoring of Physiological Parameters", IEEE Transaction on Biomedical Engineering, vol. 49, No. 10, Oct. 2002, pp. 1204-1210.

English language translation of JP 3156725 (2001), (c) Clairivate Analytics, accessed Apr. 19, 2022.

Parrinello et al., 2008 J. Cardiac Failure 14:676-686 (Year: 2008).

Pederson et al., 1978 IEEE Trans., Biomed. Engin. 25:40-48 (Year 1978).

Schaefer et al., "Monitoring Water Content of Rat Lung Tissue in Vivo Using Microwave Reflectometry",2024 Med. Biol. Eng. Comput. 42:577-580 (Year: 2004).

* cited by examiner

MEDICAL RADAR SYSTEM FOR GUIDING CARDIAC RESUSCITATION

CROSS-REFERENCE TO RELATED APPLICATION(S)

This patent application is a continuation of U.S. patent application Ser. No. 15/354,905, filed Nov. 17, 2016, titled "MEDICAL RADAR SYSTEM FOR GUIDING CARDIAC RESUSCITATION," which is a continuation of U.S. patent application Ser. No. 14/404,386, filed Nov. 26, 2014, titled "MEDICAL RADAR SYSTEM FOR GUIDING CARDIAC RESUSCITATION," Publication No. US-2015-0164417-A1, which is a 35 U.S.C. § 371 national phase application of International Application No. PCT/US2013/043337, filed May 30, 2013, titled "MEDICAL RADAR SYSTEM FOR GUIDING CARDIAC RESUSCITATION," Publication No. WO 2013/181376, which claims priority to U.S. provisional patent application No. 61/653,724, filed on May 31, 2012, and titled, "UWB SENSOR AND ALGORITHMS FOR GUIDING CARDIAC RESUSCITATION." These patent applications are all herein incorporated by reference in their entireties for all purposes.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The devices, systems and method described herein relate to the administration of cardiopulmonary resuscitation (CPR). In particular, described herein are CPR assist devices and methods that allow high-quality CPR including the rapid and accurate determination of the return of spontaneous circulation (ROSC).

BACKGROUND OF THE INVENTION

Recently revised American Heart Association (AHA) guidelines for cardiopulmonary resuscitation represent a major paradigm shift in the sequencing and priorities of the steps for providing emergency treatment using CPR, reorganizing the well-known A-B-C's (airway, breathing, circulation) to C-A-B, emphasizing circulation over airway and breathing. The key to the return of spontaneous circulation (ROSC) is the application of high-quality CPR, with compressions of adequate rate and depth, allowing complete chest recoil, minimizing interruptions in chest compressions and avoiding excessive ventilation. For adults and children, this translates to 100 compressions per minute at a compression depth of 2 inches. The new AHA guidelines also highlight the negative impact of any pauses in compression, recommending that they be minimized and if incorporated for pulse checks, limited to no more than ten seconds. The return of spontaneous circulation (ROSC) typically refers to the resumption of sustained perfusing cardiac activity associated with significant respiratory effort after cardiac arrest. Signs of ROSC include a palpable pulse or a measurable blood pressure. The return to spontaneous circulation is a recognized metric for determining the termination of resuscitation; however it is difficult to assess quickly when performing CPR.

Traditionally, a caregiver would test for ROSC by interrupting CPR and manually palpating the carotid artery to determine if a pulse is present. Detection of a pulse at the carotid artery is generally accepted as corresponding to a blood pressure of 60 mmHg systolic, the threshold for minimally viable blood pressure and flow. Unfortunately, this type of measurement is extremely subjective, time consuming to perform, and sensitive to external motion, e.g. transport by ground or air ambulance. Similarly, evaluating the quality of compressions, such as the rate and depth of compressions, typically relies on simple counting and visual estimates, both of which are inaccurate. Several CPR assist devices that incorporate accelerometer technology to measure chest compressions have been introduced but these are ineffective when the patient is on a compliant surface, such as a gurney or bed, because the applied compression often causes the compliant surface to compress rather than the patient's chest.

Although devices and methods for monitoring and providing feedback when performing CPR have been proposed and introduced, the inventor is not aware of any non-invasive systems capable of consistently and accurately determining ROSC, either alone or in combination with CPR assist tools that monitor and provide feedback on chest compression.

Thus, there is a need for devices, including CPR assist tools, that are capable of accurately and quickly indicating ROSC and/or providing feedback on chest compression, including depth and rate.

Described herein are devices, systems and methods that may address the problems identified above. For example, described herein are miniature medical radar (e.g., Ultra-wideband radio frequency radar) devices suitable for assisting with and/or managing the application of CPR and cardiac resuscitation. These devices and systems may therefore be small, rugged CPR guidance tools capable of providing feedback during the application of CPR to the rescuer, whether that individual is a healthcare professional or bystander. The feedback may allow the rescuer to optimize compressions, maximizing the probability of resuscitation.

SUMMARY OF THE INVENTION

In general, described herein are devices, systems and methods for assisting in applying cardiopulmonary resuscitation (CPR). Devices typically include an energy emitter and energy detector (which may be a single element, or may include a separate emitter and detector/receiver, a processor for analyzing the received and reflected energy, and one or more outputs for outputting an indicator of compression depth, compression frequency, and a return to spontaneous circulation. The processor may control the application of energy as well as analyzing reflected energy. Any type of energy maybe used, such as ultrasound, but including in particular, ultra-wideband energy.

The devices described herein may be configured as stand-alone devices or they may be integrated into other systems, including resuscitation systems.

For example, a stand-alone device may be configured as a rugged, wireless battery powered stand-alone device for use during manual CPR. The device may ergonomically conform to the sternum and use the intercostal spaces and/or the xyphoid to assist with alignment/placement. The device may have a selector switch for selecting the category of patient, e.g., infant, child, adult, and based on the switch position, guide the rescuer with the appropriate rates and depths, as described in greater detail herein. The device may monitor the compressions and provide feedback on compliance with AHA guidelines. In some variations, the feedback includes an audio and/or visual metronome, audio and/or visual error indicators (slow down, speed up, push harder, push softer), memory for post-CPR analysis and legal defense. It may also prompt the rescuer to pause per the American Heart Association (AHA) guidelines to evaluate the efficacy and patient response using a return of spontaneous circulation (ROSC) method as described below. Any of the devices described herein may automatically test for ROSC, either continuously, or during detected or requested periods during which compressions are not being applied. In some variations, one or more accelerometer and/or pressure transducer may also be included and used to gather additional data for correlation or for determining when to test for ROSC (e.g., by detecting with the accelerometer when compressions are not being provided).

Any of the device variations described herein may be included or integrated as part of an automatic compression system (e.g., a "thumper"). A thumper is typically a mechanical compression system that provides chest compressions per the AHA guidelines. In this variation, the devices described herein may not necessarily need to track or provide feedback on the compressions themselves as the thumper is responsible for compliance, or it may provide feedback to the mechanical compression. However, these devices may be used to test for ROSC. In some variations the devices described herein may be embedded in the head of the thumper, and may be used to evaluate the efficacy and patient response using the ROSC detection methods described herein during pauses in the application of compression.

In some variations, the devices described herein are integrated into or with a defibrillator, including either a clinical model or a public AED. Clinical defibrillators typically have two "paddles;" a devices such as that described herein may be part of or tethered to the defibrillator and the audio and/or visual feedback indicators may be embedded in the main machine, along with the defibrillator instructions/feedback. Public AED's include those with two separate patches and those with a single large patch. The energy emitter/receiver of the devices described herein (sensor) may be integrated into one of the patches or into the large patch, depending on the type of defibrillator system.

For example, described herein are devices for determining the return of spontaneous circulation (ROSC) when applying cardiopulmonary resuscitation (CPR), the device comprising: a surface configured to be placed against a patient's chest; an energy emitter and energy detector configured to emit energy from the surface into the patient; a processor coupled to the energy detector and energy emitter and configured to evaluate blood pressure from energy returning from the patient after being emitted into the patient; and an output configured to indicate the ROSC based on the blood pressure evaluation of the processor.

Any of the devices described herein may include a housing. The housing may be sealed. The housing may be configured to conform to a patient's body (e.g., chest) in an appropriate position, e.g., near the xyphoid process or in the intercostal region. In general, the surface for contacting the patient may be part of a sealed housing that includes the surface. The surface of these devices typically does not need to contact the patient directly, but may be used through clothing. In particular, the ultra-wideband variations may be used through one or more layers of clothing.

Any appropriate energy modality may be used, including ultrasound and RF energy, and in particular, UWB RF energy. The device may include a single unitary or composite energy emitter and detector, or the device may include separate emitters (transmitters) and detectors (receivers). In some variations the sensor (energy emitter and detector) is made of an ultra-wideband (UWB) transmitter and receiver configured to emit energy into a patient and to receive reflected energy. Any of these variations may include one or more antenna, such as a transmitter UWB antenna and/or a receiver UWB antenna. For example, the emitter and receiver may comprise a single antenna, or the emitter and receiver comprise separate transmitting and receiving antennas. The processor may control the application and detection (and analysis) of energy signals as described below. However, in some variations a separate controller, or an integrated controller, may be used to coordinate these functions.

The processor may be any appropriate computer processor, including dedicated or multi-purpose processors. The processor is generally connected to the sensor (emitter/receiver) and also to the output. As described in greater detail below, the processor may use reflected energy signals to track motion in the chest, determine motion corresponding to the heart (or lack of such motion) and may derive one or more indicators of heart activity, to determine if the patient has returned to spontaneous circulation (ROSC); these one or more indicators may be compared to known values, e.g., thresholds, and the results used to indicate if ROSC has occurred or has not occurred. For example, the processor may be configured to evaluate blood pressure based on the time-of-flight of energy returning from the patient after being emitted into the patient. The processor may evaluate blood pressure by determining an estimate of pulse strength from the energy returning from the patient after being emitted into the patient and compares this estimate to a threshold correlated with a known blood pressure. In some variations, the processor is configured to evaluate blood pressure by determining one or more regions showing cardiac activity based on the power spectral density of the regions and using these regions to evaluate blood pressure.

As mentioned, any of the devices described herein may be configured to determine if a patient has returned to spontaneous circulation or failed to return to spontaneous circulation. The processor may be further or alternatively be configured to determine compression rate based on energy returning from the patient after being emitted into the patient. In some variations, the process may further or alternatively be configured to determine compression depth based on energy returning from the patient after being emitted into the patient.

In variations that determine ROSC, the devices may be configured to determine this during periods in which compressions are not being applied; the device may manually determine if the patient has returned to spontaneous circulation or it may be configured to automatically detect a suspension of compressions and evaluate blood pressure when compressions are not being applied.

The devices may provide any appropriate feedback to the person applying CPR (the "rescuer"). For example, the output may be one or more of audible, visual, or tactile. For example, the output may include a notification that that the patient has or has not returned to spontaneous circulation by indicating with one or more LEDs on the device or by audibly instructing the rescuer to continue to apply compressions.

In some variations a device for determining the return of spontaneous circulation (ROSC) when applying cardiopulmonary resuscitation (CPR), the device includes: a surface configured to be placed against a patient's chest; an energy emitter and energy detector configured to emit energy from the surface into the patient; a processor coupled to the energy detector and energy emitter and configured to evaluate blood pressure from energy returning from the patient after being emitted into the patient; and an output configured to indicate the ROSC and to guide compression based on the processor's evaluation of energy returning from the patient after being emitted into the patient.

In some variations, the device for determining the return of spontaneous circulation (ROSC) when applying cardiopulmonary resuscitation (CPR), the device includes: an ultra-wideband (UWB) transmitter and receiver configured to emit energy into a patient and to receive reflected energy; a processor coupled to the UWB transmitter and receiver detector and energy emitter and configured to evaluate blood pressure based on the time-of-flight of the reflected energy returning from the patient; and an output configured to indicate the ROSC and to guide compression based on the processor's evaluation of the time-of-flight of the reflected energy.

Methods of assisting or instructing a rescuer in applying CPR are also described. In general, these methods may include applying energy (e.g., UWB RF energy), detecting and analyzing reflected energy from the patient's chest, and analyzing these reflections to determine one or more of: the return of spontaneous circulation (ROSC), the frequency/rate of compressions and the depth of compressions. The reflected energy may be analyzed to determine movement within different depths of the chest (e.g., heart movements) from time-of-flight measurements, and based on this, to determine which depth (e.g., "bins") or ranges to analyze. A pulse strength may be determined from these one or more regions and ratios representing pulse strength (e.g., maximum amplitude versus mean amplitude) may be compared to a threshold value corresponding to a known blood pressure. This comparison may therefore provide an evaluation of the patient's blood pressure, which may be used to determine ROSC.

For example, described are methods of determining the return of spontaneous circulation (ROSC) when applying cardiopulmonary resuscitation (CPR), the method comprising: placing a device against the patient's chest, wherein the device comprises an energy emitter and energy detector configured to emit energy from the surface into the patient and a processor coupled to the energy detector and energy emitter; performing CPR on the patient; emitting energy from the device into the patient's chest; detecting energy reflected from the patient's chest; evaluating the patient's blood pressure from the energy reflected from the patient's chest; and indicating based on the evaluated blood pressure if the patient has returned to spontaneous circulation.

Placing the device may include placing the device on the patient's chest before initiating CPR. As mentioned, the device may be placed over clothes, or against a patient's bare chest.

The method may be used when emitting ultra-wideband radio frequency energy into the patient, or using other energy forms, including ultrasound. The step of detecting energy reflected from the patient's chest may comprise sampling at different times to determine values at different depths into the body. For example, evaluating the patient's blood pressure comprises determining time-of-flight of the reflected energy. Evaluating the patient's blood pressure from the energy reflected from the patient's chest may comprise estimating when compressions are not being applied so that the ROSC analysis can be performed during this period.

Evaluating the patient's blood pressure from the energy reflected from the patient's chest may comprise determining an estimate of pulse strength from the reflected energy and comparing the estimate of pulse strength to a threshold correlated with a known blood pressure. Evaluating the patient's blood pressure from the energy reflected from the patient's chest may comprise evaluating blood pressure by determining one or more regions showing cardiac activity based on the power spectral density of the regions and using these regions to evaluate blood pressure.

In any of the methods described, compression rate may be determined based on the reflected energy, and an indicator of compression rate may be output. Similarly, compression depth may be determined based on the reflected energy, and an indicator of compression depth may be output.

Also described herein are devices for assisting in CPR by monitoring and reporting compression rates and/or depth using UWB. For example, a device for assisting in CPR by providing feedback on compression rates and/or depth may include: a surface configured to be placed against a patient's chest; a UWB energy emitter and energy detector configured to emit UWB energy from the surface into the patient; a processor coupled to the UWB energy detector and energy emitter and configured to evaluate blood pressure from UWB energy returning from the patient after being emitted into the patient; and an output configured to indicate compression rate and/or depth based on the motion of tissue beneath the reflection of the UWB energy from tissue beneath the surface. In some variations, the device includes a sealed housing including the surface. The device may be configured to automatically and continuously monitor compressions.

In some variations, the UWB energy emitter and detector comprise an ultra-wideband (UWB) transmitter and receiver configured to emit energy into a patient and to receive reflected energy. The emitter and receiver may comprise a single antenna, or the emitter and receiver may comprise separate transmitting and receiving antennas.

The processor may be configured to evaluate compressions based on the time-of-flight of energy returning from the patient after being emitted into the patient. In some variation, the processor evaluates compressions by determining an estimate of pulse strength from the energy returning from the patient after being emitted into the patient and compares this estimate to a threshold correlated with a known blood pressure. In some variations, the processor determines the amount of shift (motion) of tissue beneath the sensor based on the change in depth of similarly reflective regions. In some variations, the processor is configured to evaluate compressions based on the power spectral density of the regions and using these regions to track motion. As used here evaluating compressions may include estimating rate and/or depth of compressions.

BRIEF DESCRIPTION OF THE DRAWINGS

In FIG. 4, an actual measured trace for cardiac motion pulse strength is compared with a predetermined threshold of 60 mmHg systolic pressure (line at −0.8); the blood pressure in the experimental animal was held at below 60 mmHg; in FIG. 5, the blood pressure was held above 60 mmHg.

DETAILED DESCRIPTION OF THE INVENTION

A medical radar system may be used to enhance the efficacy of delivery of cardiopulmonary resuscitation (CPR). In particular, the devices and methods described in detail below refer to ultra-wideband (UWB) medical radar systems, however, it should be understood that these principles may be applied to other medical radar systems, including ultrasound systems.

UWB radio frequency (RF) radar is an active imaging technology similar in functional concept to ultrasound but is based on electromagnetic, rather than sonic energy. In practice, a UWB Medical Radar may emit a micro-pulse of electromagnetic energy, which propagates into the human body. As the energy enters the body, small amounts of the incident energy are reflected back to the device. The reflections are primarily a result of the differences in dielectric properties of the underlying tissues and organs. The reflected energy is received and processed using signal processing algorithms to extract information on the type, location, size, and relative movement of the illuminated tissues and organs. The radar's extremely narrow transmitted pulse (e.g., 150 ps FWHM) along with it fine timing resolution (e.g., 250 ps) and variable interrogation range (typically 1 cm to 50 cm for torso-based applications) allows the sensor to accurately detect, track, and measure small internal movements throughout the chest.

Figure 1A:
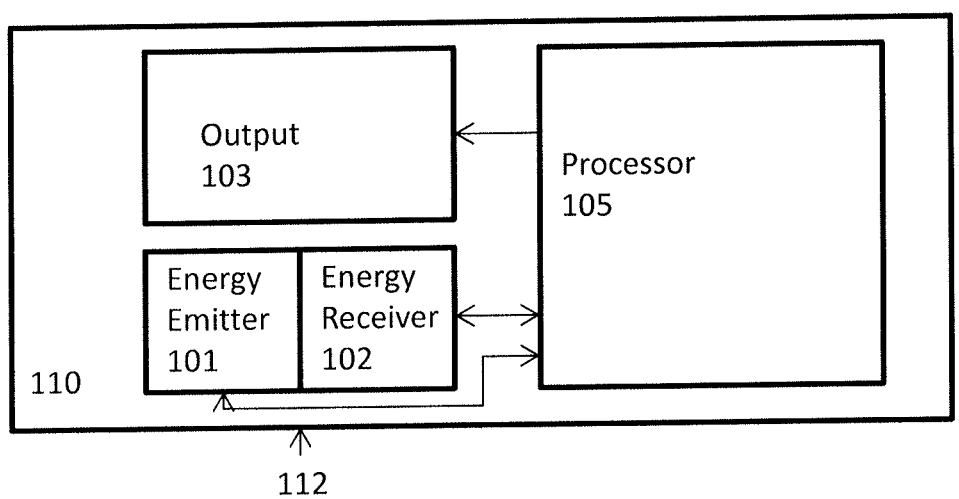
FIG. 1A is a schematic of a medical radar device for assisting in applying cardiopulmonary resuscitation (CPR).

FIG. 1A illustrates one generic variation of a device for assisting/instruction CPR. In this example the device includes a processor 105 that is functionally connected to, and may control, an energy emitter and energy reliever 101, 102. The receiver and transmitter may be separate or unitary, and may include additional elements (e.g., antenna, resonators, filters, etc.) not illustrated in this schematic. The processor may also be connected to the output 103. The entire device may be housed within (and sealed within) a housing 110. The housing may include a surface 112 to be placed against the patient's chest, directing the energy into the patient's chest.

Figure 1B:
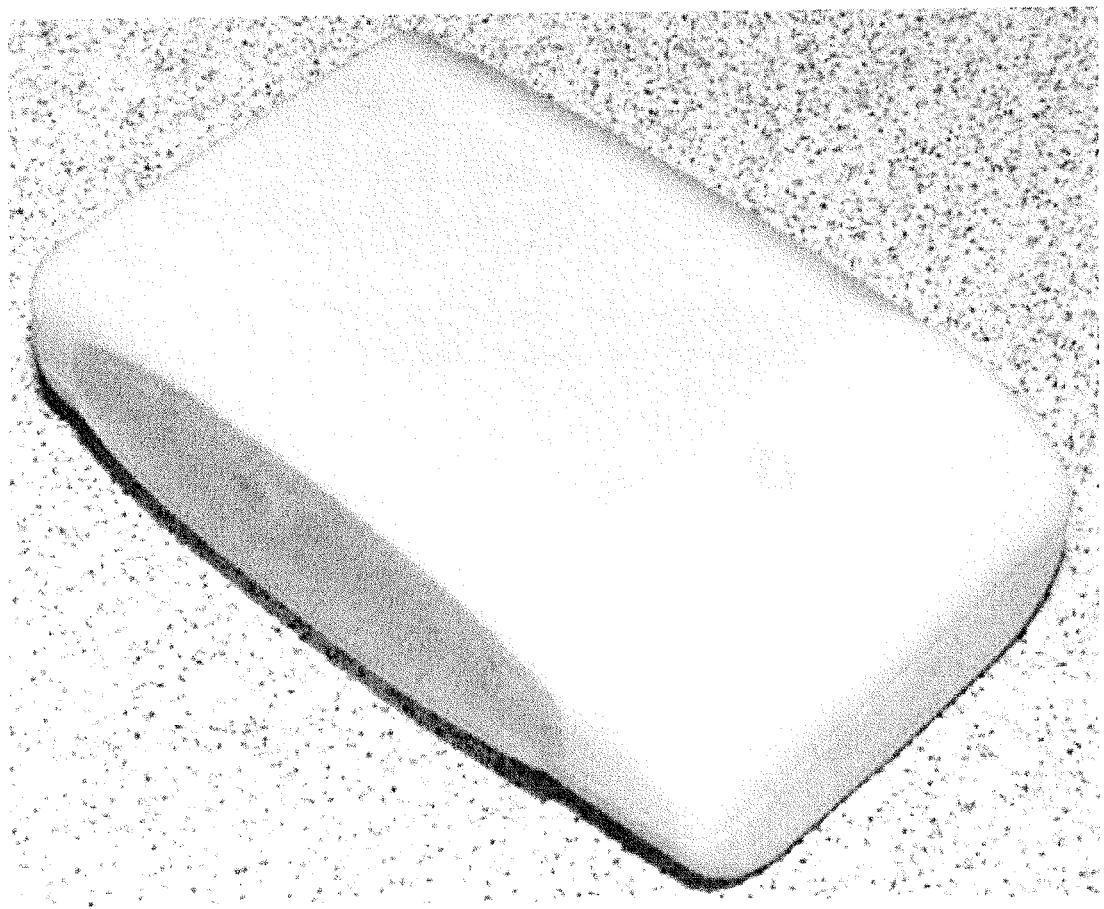
FIG. 1B is an example of a UWB medical radar device having a visual indicator (LED) for visual feedback indicating that a patient has or has not resumed spontaneous circulation based on a predetermined threshold (e.g., corresponding to a blood pressure of 60 mmHg systolic).

FIG. 1B shows another variation, configured as a UWB medical radar system. In this example, the device is extremely small and lightweight, measuring 2.875"×1.875"× 0.875" and weighing less than 2 oz. The assembly shown includes the case (housing), radar circuitry, separate transmit and receive antennas, and a 1200 mAhr Li-Ion battery, providing over 4 hours of continuous operation. The case may be ergonomically designed to fit snuggly on the chest, contouring to the shape of the sternum between the jugular notch and the xiphoid process. The case is resistant to fluids and sufficiently strong enough to protect the internal circuitry and minimize flexing or deformation during compressions.

In general, the medical radar devices may be based on basic time-of-flight principles using a variable range gate, allowing it to collect data from a wide range of depths within the human body. Per equation 1, a time of flight UWB radar works by sampling the signal present at the receiving antenna a precise time after transmission of an impulse where the time difference between the transmitted pulse and sampling of the received signal corresponds to the range to the desired target in the propagating medium.

$$\text{Range} = \frac{ct}{2\sqrt{\varepsilon_r}}: \quad [1]$$

Where: c==speed of light, t=time of flight, $\varepsilon_r$=relative dielectric constant of the media.

Given a real-world environment containing numerous static and dynamic targets, each transmitted pulse will result in a continuous received signal at the receiving antenna where the sampler is responsible for providing range and thus, target discrimination, allowing the system to isolate individual targets. An ideal sampler will sample the signal present at the receiving antenna, passing that signal to the receiver at the specified time with minimal distortion while effectively blocking all signals present at the receiving antenna at other times. In practice, the set of desired interrogation depths encompassing the organs of interest is divided into a series of range bins where the number and width of the range bins is a function of the radar's radial resolution.

Figure 2:
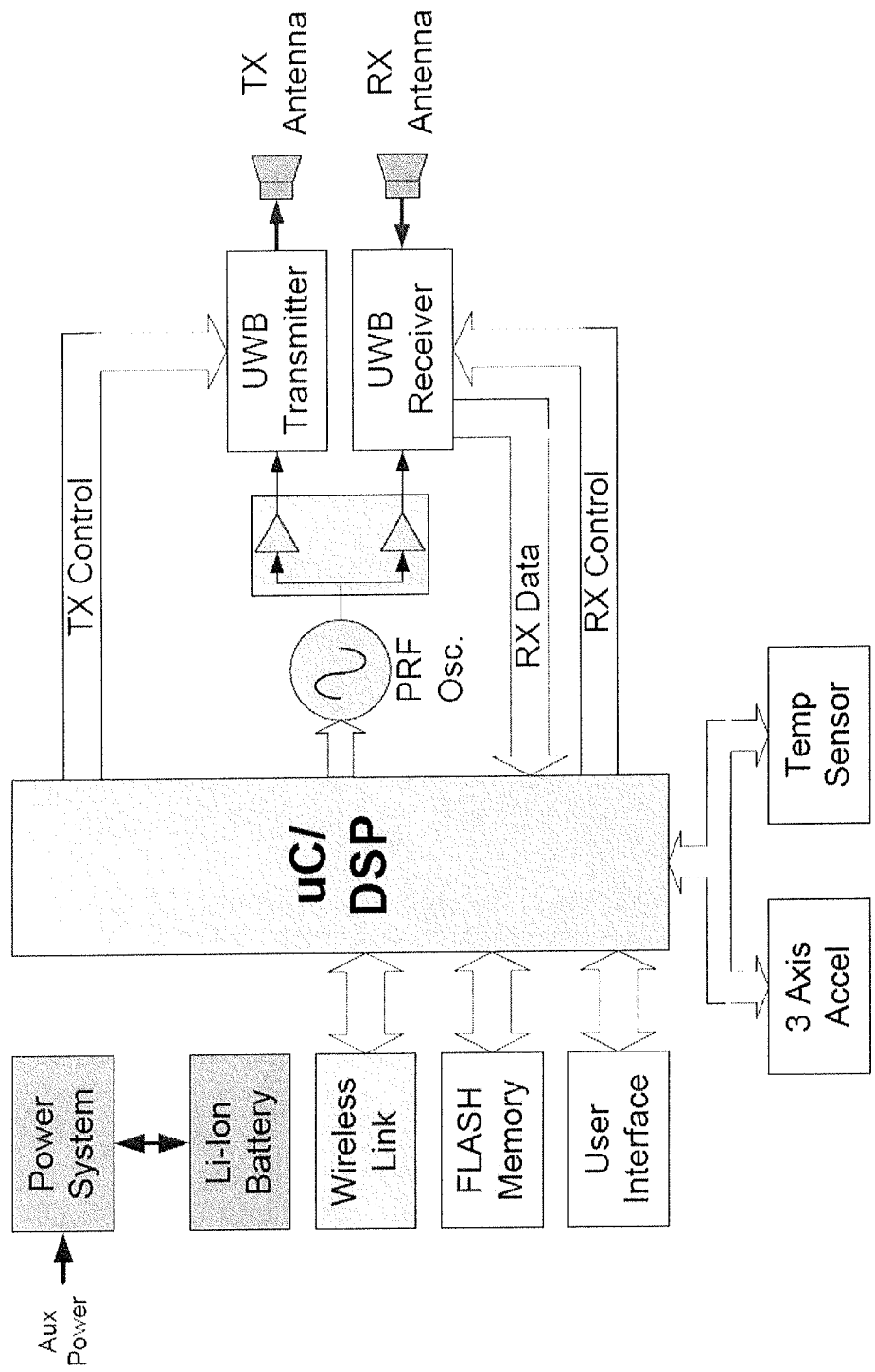
FIG. 2 is a block diagram of one variation of a UWB medical radar device for assisting in applying cardiopulmonary resuscitation (e.g., determining the return of spontaneous circulation).

As shown in FIG. 2, an exemplary device such as the one shown in FIG. 1A may consists of an embedded processor, a communications link, non-volatile memory, a multi-color LED (output), a precision timing circuit, a UWB transmitter, a UWB receiver, a multi-axis accelerometer, a thermometer, and battery management/charging circuitry.

The selection of a specific embedded processor depends on the target system configuration with a more capable device required for the higher computational load inherent with autonomous operation. If the sensor is connected to another medical device, e.g. a vital signs monitor or defibrillator, it is possible to off-load some of the signal processing to that device, reducing the requirements on the sensor's embedded processor. The most recent prototype uses a 64 pin, 32 bit microcontroller. This device has sufficient I/O, Flash memory, and computational capabilities to manage all radar, UI, communication, and battery functions as well as process and store the radar and accelerometer data. Various communication links may be used, including wired (e.g., RS232, USB 1.1 and 2.0) and wireless (e.g., 928 MHz ISM and Bluetooth) where the selection of the link depends on the desired system configuration and intended use model.

The precision timing circuit, UWB transmitter, and UWB receiver may be used as known; the timing system may be configured to have a low relative jitter between the transmitter and receiver paths, as jitter translates into noise and reduces receiver sensitivity. In some variations, the main features of the timing circuit are a common pulse repetition frequency (PRF) oscillator, nominally operating at 16 MHz, and a low jitter/skew clock buffer sourcing both the transmitter and receiver timing paths. Both the transmitter and receiver timing paths may include a delay line and buffer. In one variation, both paths use an 8 bit, 250 ps resolution programmable CMOS delay line for maximum flexibility but in a production design, a fixed delay line could be substituted for the programmable model in either one but not both of the transmitter or receiver paths to reduce power consumption and cost. One path may contain a variable delay line of some sort to allow the sensor to scan across a range of depths or dynamically focus on specific anatomical structures. From practical experience, it may be desirable to control the range setting by varying the transmitter delay, i.e. place the programmable delay line in the transmitter path, rather than the receiver delay as any dynamic changes to the receiver configuration can introduce noise.

The timing signal from the transmitter path may be fed to the UWB transmitter to generate an impulse. For medical applications, a bipolar pulse having a pulse width of 120 ps-160 ps FWHM and amplitude of 5 to 8 volts peak-to-peak prior to filtering and differentiation by the transmitter antenna produces good results. Several impulse circuits have been evaluated in the context of the devices described herein, including those featuring a step recovery diode (SRD) and high-frequency transistors, demonstrating the ability to generate either unipolar (positive or negative peak) as well as the more desirable bipolar pulses. In some variations, transistors would most likely be selected over SRD's as they are much less expensive.

Figure 3:
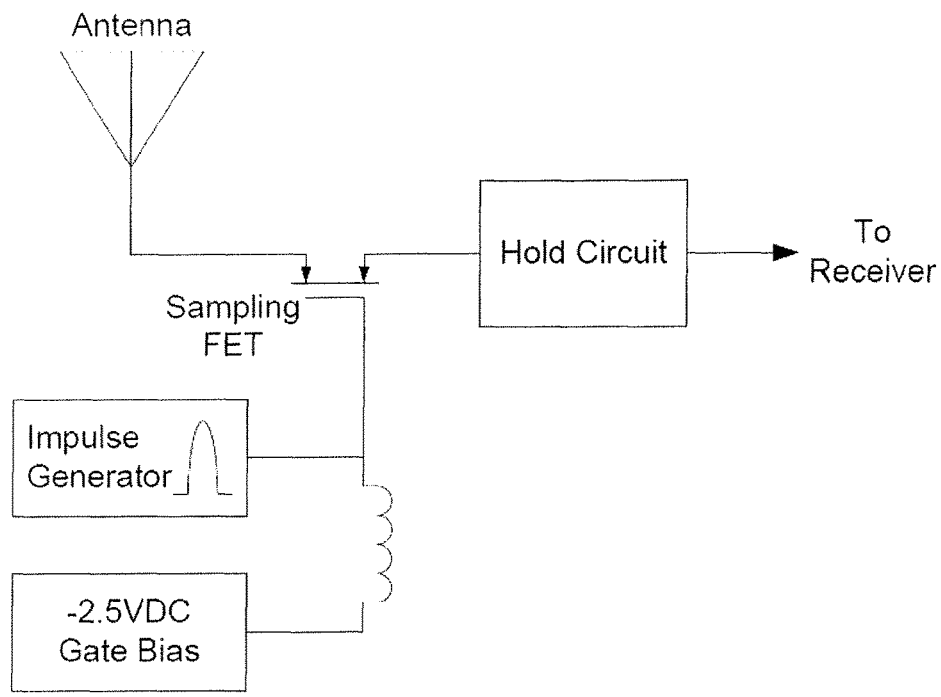
FIG. 3 shows one variation of a FET based UWB sample and hold circuit.

In FIG. 1B, the UWB receiver consists of two sections, the UWB sample and hold and the low frequency (or baseband) receiver. A simplified block diagram of one example of a UWB sample and hold circuit is shown in FIG. 3. In FIG. 3, the sample-and-hold circuit is a high speed switch triggered by a second impulse generator. Although other sampler designs may be used, using a FET for the switching element may provide significantly better performance over the Schottky diode-based designs commonly found in the literature. In practice, a commercially available K-band N-channel HJ-FET with a gate bias of −2.5V and a trigger impulse of 200 ps-250 ps at 2.5 Vpp produces a more consistent on-time impedance and better off-time isolation. The impulse generator may be a de-tuned version of a design used in the transmitter and is fed by the output of the receiver delay line.

The output of the FET switch may be connected to the hold circuit which is responsible for integrating the returns from a single depth over numerous transmitted pulses. For example, given a PRF of 16 MHz, 40 discrete depths, and a scan rate of 50 HZ, the sampler will transfer returns to the hold circuit from 8,000 transmitted pulses per each discrete depth. The hold circuit may average those 8,000 returns yet reset quickly when the sensor changes the timing to interrogate the next discrete depth, dumping all stored charge from the previous depth. In the illustrated example, an active discharge circuit has been added to the hold circuit that is energized anytime the sensor changes depths.

In the exemplary device shown, the low frequency portion of the receiver is connected to the output of the hold circuit and amplifies, filters, and digitizes the received signals. For a CPR application and using the operating parameters from above, an example of an appropriate receiver bandwidth is 5 kHz (e.g., 2.5 times the rate of change of the depths) with a fixed voltage gain of 100. Following the fixed gain section is a programmable gain amplifier (PGA) and a 16 bit analog-to-digital converter (ADC). The PGA allows the sensor to optimize the amplitude of the received signal, accounting for variations in patient anatomy, and it allows the sensor to increase the receiver gain for increasing depth to compensate for increased losses. The ADC digitizes the integrated, amplified, and filtered returns. The ADC may oversample the data typically by a factor of 8× or 16× to reduce random noise in the signal. Depending on the ADC selected and its features, the oversampled data is either averaged internally by the ADC or after transfer to the processor. Once transferred to the processor, algorithms extract the desired data.

In any of the devices and methods described herein, the devices may be self-contained, so that they may monitor the patient with a single housing, and do not require a separate sensor, plate, electrode or reference to be placed on a second or additional site on the body.

Sensor Methods

Figure 9:
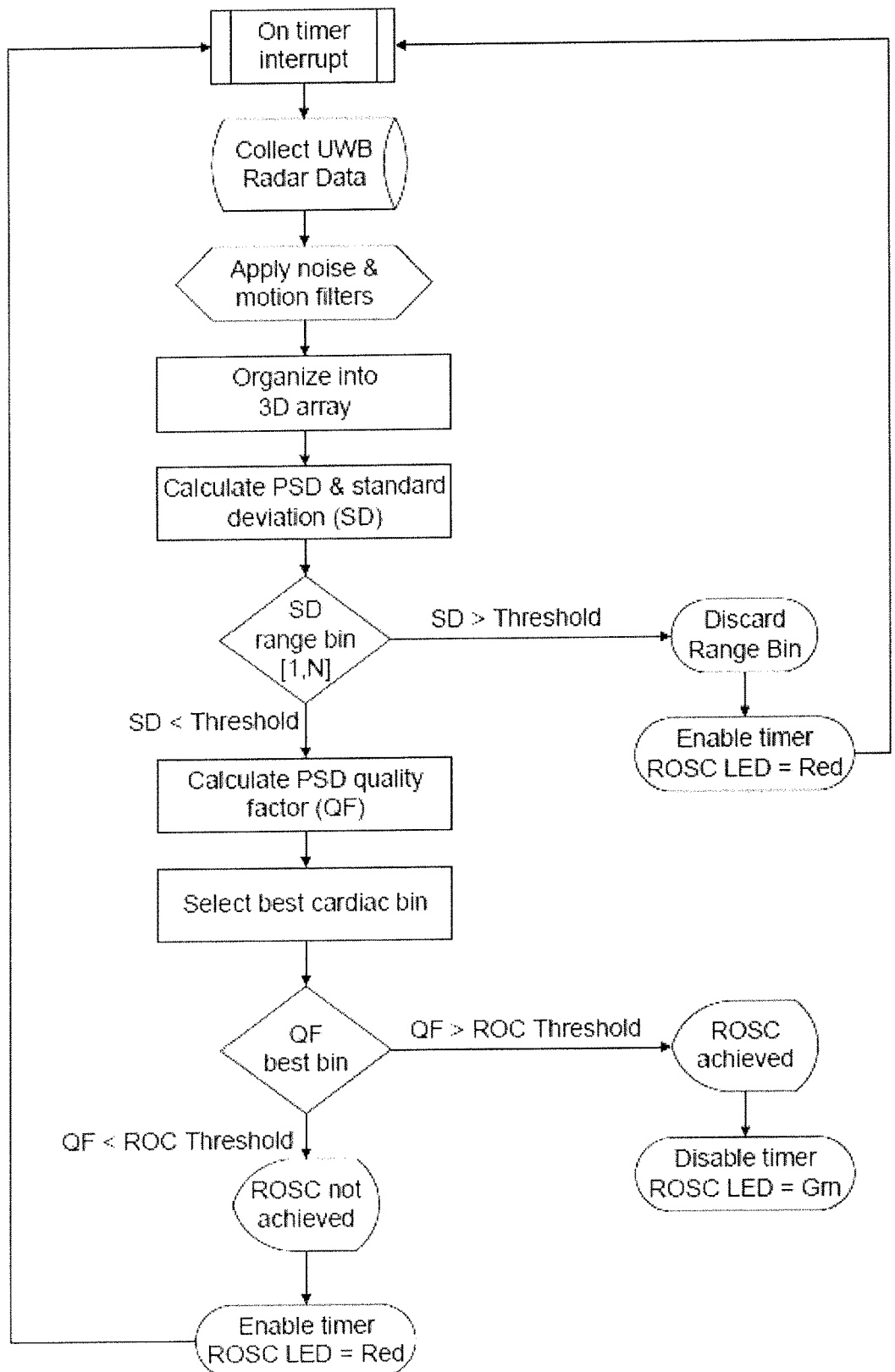
FIG. 9 is a flowchart illustrating one method of determining ROSC using a medical radar system as described herein.
Figure 10:
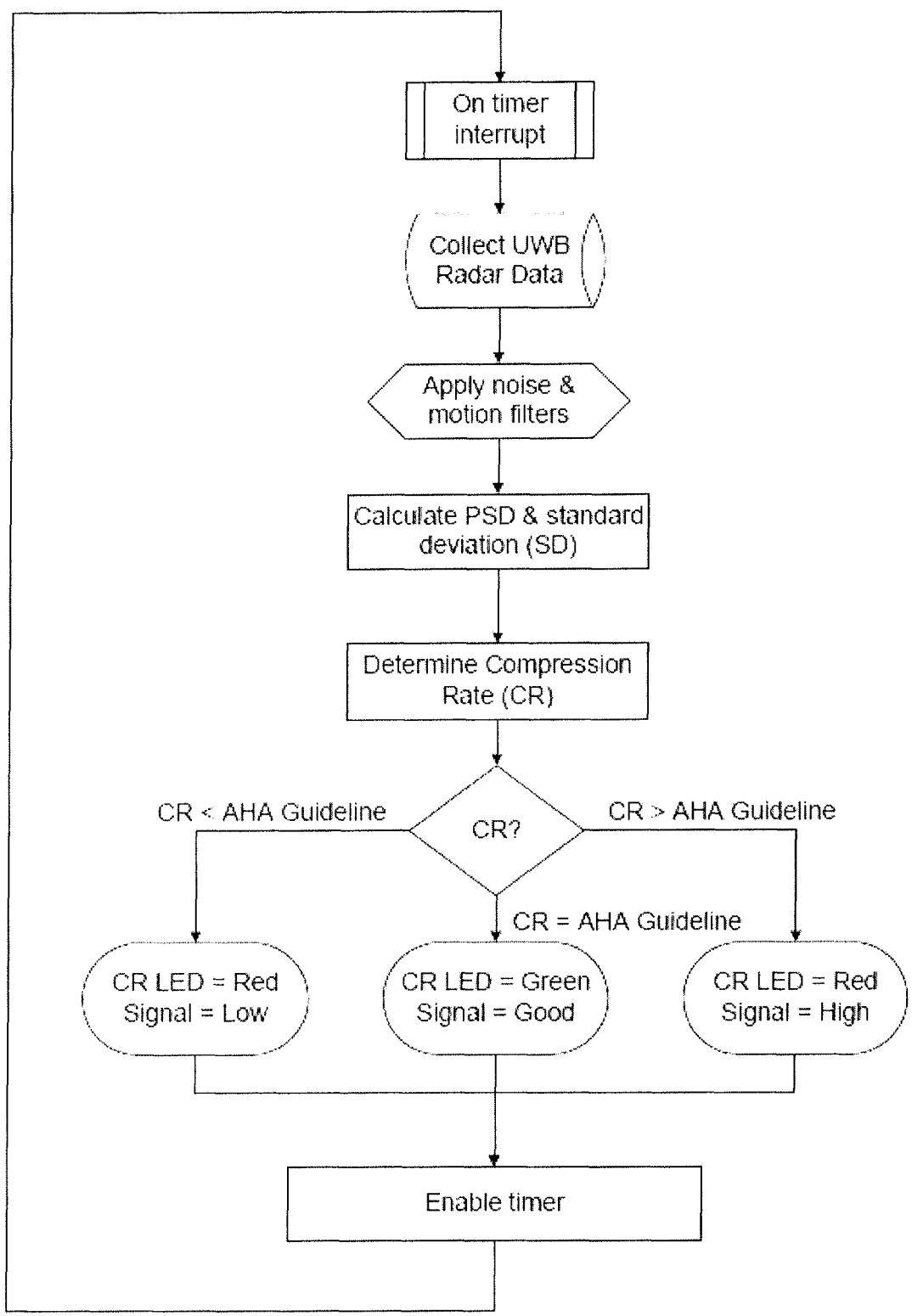
FIG. 10 is a flowchart illustrating one method of determining compression rate using a medical radar system as described herein.
Figure 11:
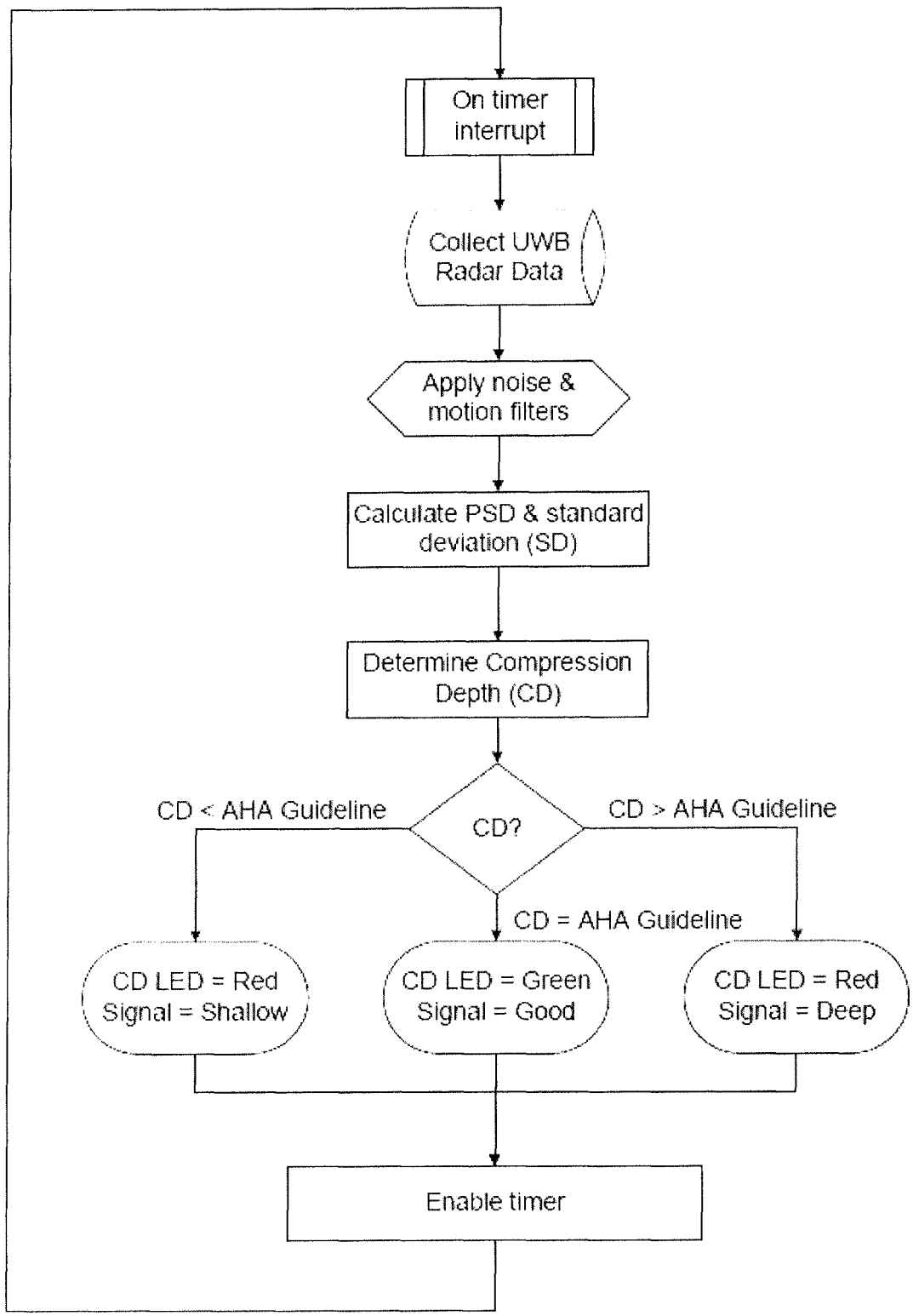
FIG. 11 is a flowchart illustrating one method of determining compression depth using a medical radar system as described herein.

Described herein are specific signal processing methods that may be used to determine heart motion from reflected energy and may determine if a patient has returned to spontaneous circulation, examine the rate of compressions being applied, and examine the depth of contractions being applied. FIGS. 9-11, described in more detail below, illustrate these methods. In some variations the devices and systems descried herein may be configured to execute these methods, using software, hardware and/or firmware. Thus, these methods may be described as processes and/or as algorithms. Further, although the examples provided herein are directed to ultra-wideband applications, it should be understood that these same principles can be applied to any reflected energy, including ultrasound.

For example, signals from UWB radar data that non-invasively probes a patient's chest may be processed to determine information about the relative motion (e.g., relative to the device, and/or to other biological structures such as the chest wall). These methods may be able to extract information on heart wall motion and changes in the chest cavity geometry from the data to provide actionable information concerning the presence or absence of viable blood flow and therefore derive information that can be provided as feedback on the application of CPR.

In one variation, a CPR algorithm may include evaluation of blood pressure, and measurement of compressions (e.g., frequency and depth). Evaluation of blood pressure provides an accurate indication of the return of spontaneous circulation (ROSC). As used herein an evaluation of blood pressure does not require a measurement of blood pressure, but may instead be performed by comparing a measurable value derived from reflected energy and dependent upon heart and/or blood motion with a reference value that is derived from a known blood pressure. However, in some variations, the device or system (e.g., using a processor) may be used to determine an estimate of blood pressure, or an estimate of a blood pressure range (e.g., above or below a blood pressure value).

To test for ROSC, a device including a sensor for emitting energy and detecting reflected energy collects data from the patient during a short pause in compressions being applied while performing CPR. In some variations the pause may be signaled to the rescuer by audible and/or visual indicators on the sensor or on resuscitation equipment in communication (wired or wireless) with the sensor. In some variations the pause is automatically detected by the sensor. The length of the pauses and intervals between pauses may be under control of the device (e.g., the processor), allowing the sensor to be easily updated as AHA guidelines evolve. For example, firmware on the sensor may be updated to modify any of the methods described herein.

During a pause, the sensor may reduce the scan range of the radar to focus on the heart with typical scan ranges of 1-5 cm for children under eight years of age and 2-10 cm for children over eight years of age and adults. These range intervals ensure that the anterior wall of the heart is within the range of the radar. Thus, in some variations the device may include a switch or other control to select infant/child/youth/adult or simply patient size (small/medium/large).

This focused data may be first filtered to remove all static returns and isolate the motion data within an appropriate frequency range of interest, typically corresponding to 30 BPM to 150 BPM. If motion data within the range of expected rates is not detected, the device may indicate that there is no heart activity and immediately signal the rescuer to resume compressions. If motion data within the range of expected rates is detected, the data containing heart wall motion may be processed to provide information on the changes in the patient's blood pressure. An ROSC determining algorithm may compare the results to a threshold previously selected to determine if the motion corresponds to blood pressure is above or below the threshold. For CPR, the threshold may be set to 60 mmHg systolic, where pressures below this limit implies a lack of viable circulation and pressures above this limit implies a return of spontaneous circulation. This information allows rescuers to better direct continued aid and if warranted, initiate advanced resuscitation protocols. The algorithm may be composed of at least four components: preprocessing, gross motion artifact detection, baseline analysis, and computation of the pulse level. As a proof of principle and for purposes of FIGS. 4-7, an algorithm was developed in Matlab and results calculated by post-processing the data. However, a processor may be configured to perform a similar method as part of an embedded platform for real-time functionality.

Regarding FIGS. 4-7, the algorithm used to generate these examples was developed with data collected from a series of IACUC-approved experiments using a porcine model. Data was collected from the animals while cardiac rate and contractility state were varied using pacing and pharmacological agents. The data was processed to determine features within the radar signal that differentiate between cardiac motion associated with a palpable carotid pulse and no palpable carotid pulse. The reference device in these studies was an arterial BP line, and the reference threshold used for determining viable carotid pulse was set to 60 mmHg systolic, corresponding to a palpable carotid pulse typically indicative of viable circulation. The blood pressure algorithm was based on spectral techniques and included the development of a statistical model that was evaluated using receiver-operator characteristic curves (ROC) to determine an appropriate threshold for the radar data.

FIG. 9 illustrates one variation of a method of testing for the return of spontaneous circulation consistent with the steps described below.

In step 1 ("preprocessing"), a focused oversampled data set may be first averaged over the samples within each range bin to reduce the random noise. The resultant data matrix may have the dimensions of range bins (rows)×time samples (columns), where each row of range bins corresponds to a single scan across the entire anatomical region of interest. Next, the matrix may be partitioned into time segments that overlap. For example, the matrix may be partitioned into 5 second segments that overlap by 4 seconds, resulting in 1 second of new data per 5 second segment of data. Each segment may then be filtered (e.g., with a moving average filter) to further reduce high frequency noise. Once filtered, the data may be down-sampled to reduce HF noise as well as reduce the size of the data set to improve processing efficiency.

In step 2, ("motion artifact detection"), each filtered segment may be analyzed for non-cardiac motion artifacts. This may be accomplished by combining multiple range bins and calculating the standard deviation of the motion rates against a preset threshold value. If the calculated value of standard deviation is greater than the threshold, there is either no cardiac activity or other motion is masking the cardiac motion. Segments with a standard deviation greater than the threshold can be discarded. Data provided by an integrated accelerometer can also be used to minimize the effects of motion on the UWB signals.

In step 3 ("baseline depth calculation"), segments with a standard deviation less than the threshold are analyzed to determine which range bins, i.e. depths, have the strongest cardiac returns and should be used for further processing. This may be done by looking at the spectral content of the signal at each discrete depth in the segment. The power spectral density (PSD) of each bin can be calculated using an FFT and the mean and maximum of the PSD within the cardiac range (e.g., 30 beats per minute (BPM) to 150 BPM) can be determined. A quality factor of each bin may be calculated, by taking, for example, the ratio of amplitude of the strongest frequency component and the mean amplitude of all frequency components. Other quality factors may be used. For example, the quality factor may be a maximum or an average maximum, or normalized maximum, of the frequency component. Bins with high cardiac ratios can be interpreted as having strong cardiac signals while bins with low ratios can be interpreted as having weak cardiac signals. The ratios may be sorted in descending order, and the bins with the top three ratios designated as having the best cardiac returns can be used for all subsequent processing. The baseline depth may be recalculated every 15 second or whenever a motion artifact is detected, allowing the sensor to effectively compensate for changes in the location and/or orientation of heart as well as any drift in the electronic circuitry.

In a fourth step ("computation of the pulse strength"), a computation of pulse strength utilizes the quality measure previously calculated in the baseline depth calculation. The theory is that as the blood pressure drops, the ratio of the maximum amplitude versus the mean amplitude will approach unity, corresponding to decreased cardiac contractility. Using the data collected from numerous animal models and analyzed through development of ROC curves, a threshold for the cardiac ratio can be selected that corresponds to a blood pressure of 60 mmHg systolic. Once the algorithm determines that a single segment or several consecutive segments has fallen below this threshold, the sensor can signal an alert the rescuer using audible and/or visual indicators, indicating that the blood pressure is below 60 mmHg and compressions should be initiated immediately.

Figure 5:
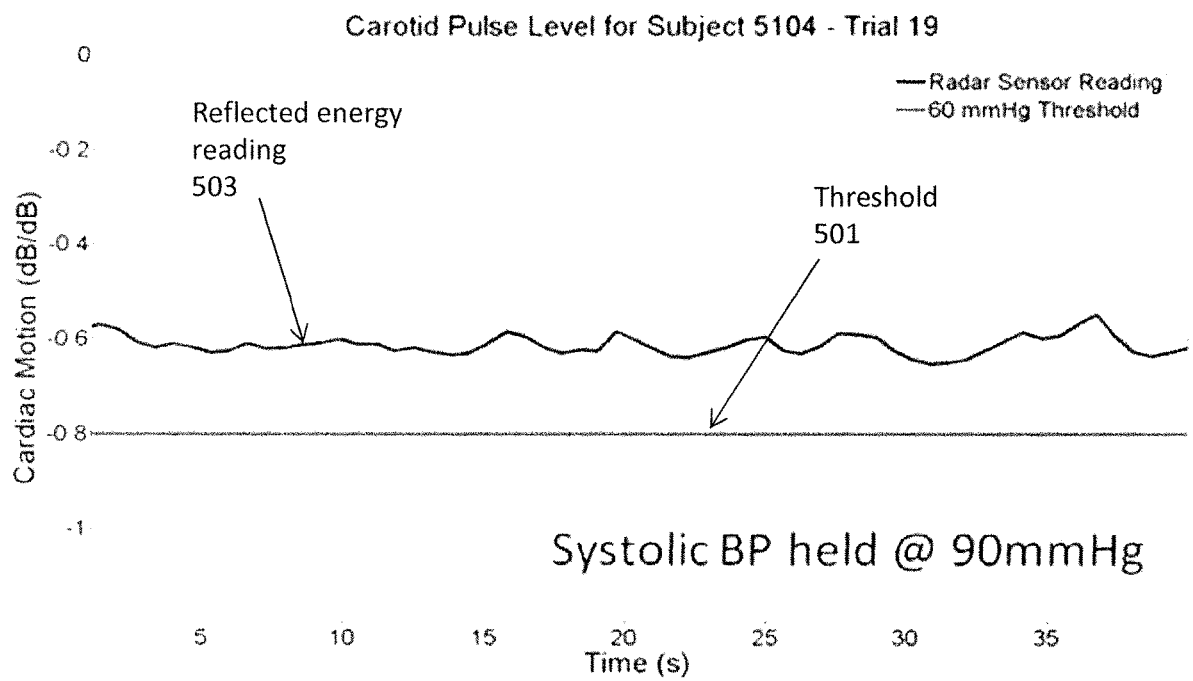
Figure 6:
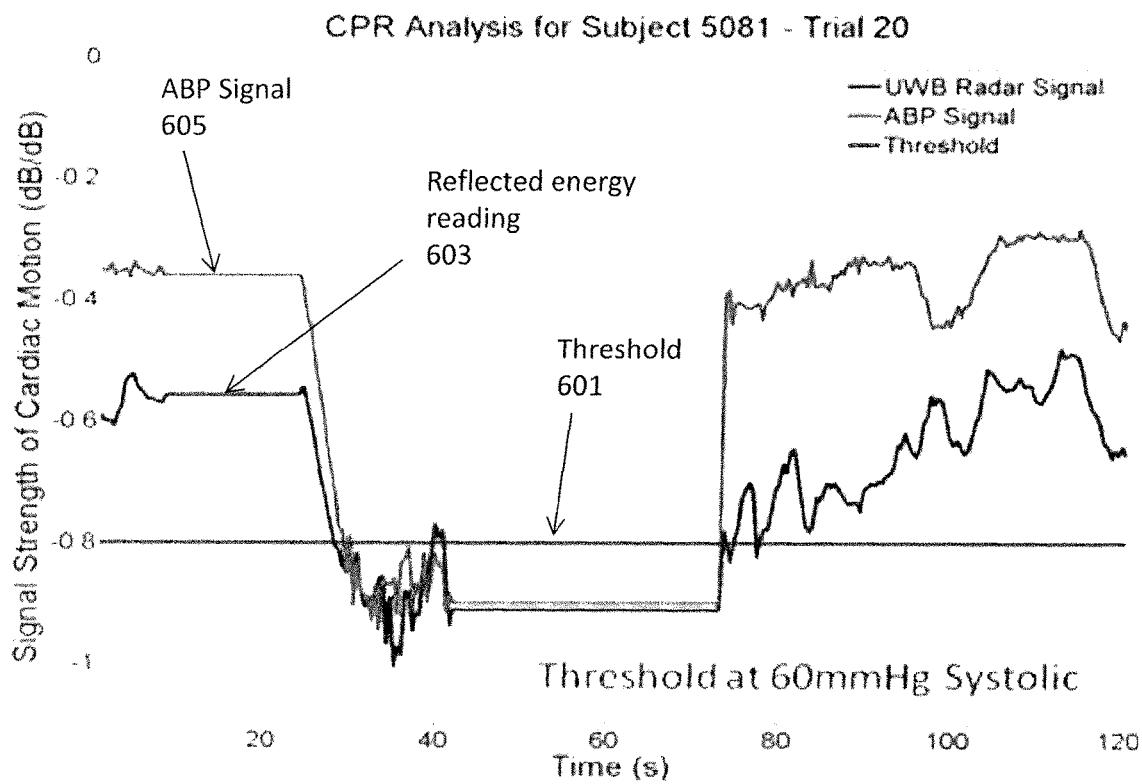
FIG. 6 shows a graph comparing the UWB system with a measure of arterial blood pressure; for comparison, the threshold corresponding to 60 mmHg is also shown.
Figure 7:
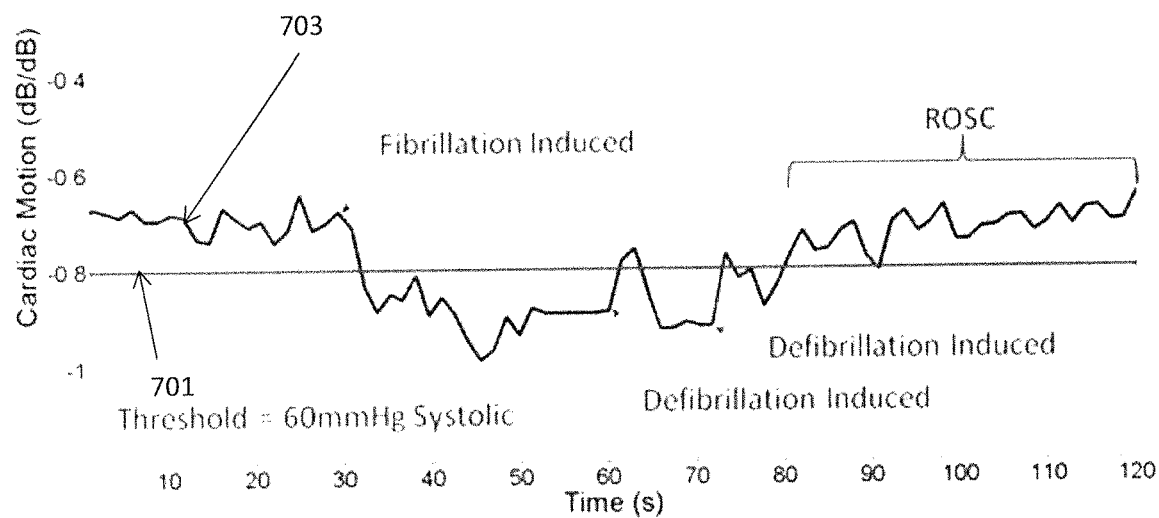
FIG. 7 illustrates the effect of the UWB determination of cardiac motion pulse strength in an animal in which fibrillation was induced, following by two rounds of defibrillation; the threshold corresponding to 60 mmHg is also shown.

FIGS. 4 through 7 illustrate the results of blinded tests with the sensor and ROSC algorithm on data collected from porcine models. As mentioned, in some variations, it is not necessary that the sensor and associated ROSC algorithm calculate absolute blood pressure but instead detect changes in blood pressure that exceed a pre-programmed threshold. In FIG. 7, for example, an animal exhibiting normal sinus rhythm was placed into ventricular fibrillation (VF), and subjected to a first defibrillation shock, but did not recover and was given a second defibrillation shock 13 seconds after the first shock, after which it finally recovered. The trace produced by the UWB medical sensor accurately cataloged the various cardiac states.

Figure 4:
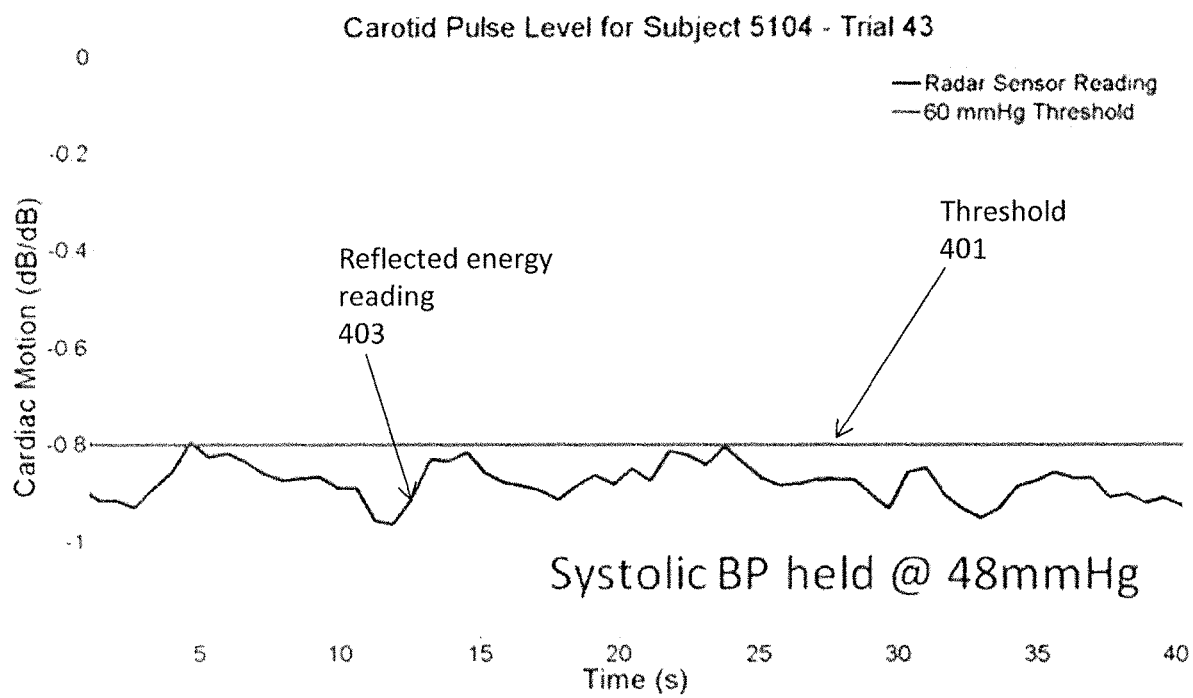
FIGS. 4 and 5 show examples of graphs illustrating the evaluation of blood pressure from energy returning from the patient after being emitted into the patient from a device such as the one shown in FIG. 1B.

FIG. 4 graphically illustrates the results of the method above when the blood pressure following CPR is below the accepted threshold for indicating ROSC. In this example, the quality factor ratio is calculated over time (40 sec) 403 and compared to the threshold value 401 determined for 60 mmHg. As a result the cardiac motion would be reported by the device as being insufficient for ROSC, and further compressions would be indicated.

Alternatively, FIG. 5 illustrates an example where the quality factor for the reflected energy 503 is above the threshold over the time examined, and the device would indicate that ROSC has been achieved (e.g., compressions may stop).

FIG. 6 shows a situation in which the heart was stopped, and then re-started, to compare the sampled and analyzed reflected energy readings 603 with an actual Arterial Blood Pressure signal (ABP) 605. As shown, during the period where the heart was stopped, the reflected energy reading was primarily below the threshold (−0.6) determined from 60 mmHg; after the heart rate was restored, the value of the quality factor determined from the reflected energy of the heart was above this threshold.

As mentioned, FIG. 9 illustrates one example of a method for indicating ROSC. A device or system as described herein can perform this method. The four steps described above may be incorporated into this method. For example, UWB reflected information may be collected and filtered, and organized into a 3D array by depth and time and repetition number. The power spectral density may then be calculated, and standard deviations determined from this data. The bins may then be analyzed to determine if the standard deviation is above or below a threshold; if they are above, they may be discarded (if all of them are above, there the test for ROSC fails, and the device may so indicate). A PSD quality factor measurement may be made for the bins that have a SD<threshold and the bins may be ranked by this quality factor. The quality factor (QF) for the best bins (e.g., highest ranking by power spectral density or otherwise) may be compared to a threshold that corresponds to a predetermined blood pressure value accepted as a threshold for determining ROSC. For example, the threshold value may correspond to the value of a typical (average) QF when the blood pressure is 60 mmHg systolic. If the best of the quality factors is greater than this threshold then the ROSC has been achieved and the device may indicate this; if not, the device may instead notify the user to continue compressions. This process may be reiterated/repeated for some predetermined time period (e.g., 5 sec, 10 sec, 20 sec, 30 sec).

The devices and systems described herein may also include methods of determining the quality (e.g., depth) or frequency of compressions being applied during CPR. For example, the devices may also be configured to determine compression frequency and/or depth by measuring the actual movement of the chest and/or heart, rather than the motion of the hands or device.

For example, described herein are methods of analyzing compression. Compression algorithms to measure the rate and depth of compression may be relatively simple, and may take advantage of some of the same steps/processes described above for determining ROSC. In some variations the device may be configured to collect data from the patient for evaluation of compressions outside the time frame of the pauses in compressions used to determine the presence or absence of spontaneous circulation (e.g., while performing compressions). Audible and/or visual indicators on the sensor or on resuscitation equipment in communication (wired or wireless) with the device may signal the rescuer to initiate compressions. During this time, data may be continuously collected across an expanded range of depths and processed to measure the rate and depth of compressions, providing unique audible and/or visual indicators that assist the rescuer in optimizing the compressions to better meet the AHA recommendations. Unlike the ROSC algorithm, this algorithm may not focus exclusively on the heart and instead may use an expanded range of depths to gather motion data from a large volume of the chest, increasing accuracy and minimizing the effects of external factors. The compression algorithm consists of three main components-preprocessing, compression rate calculation, and displacement calculation.

A first step of this method, ("preprocessing") may be very similar to the preprocessing performed by the ROSC algorithm except that down sampling is consistently applied to the time domain data. Down sampling may reduce the amount of data, allowing the processor to run at slower speeds and conserve power. This reduction in data is possible with the extreme strength of the compression returns.

In a second step ("compression rate calculation") the PSD may be calculated for the filtered and segmented data produced by the preprocessor for each range bin or depth. A peak detector may determine the frequency component with the maximum amplitude for each of the range bins and the mean and standard deviation of the strongest frequency components across all bins are calculated. The mean represents the compression rate while the standard deviation provides a confidence factor to help minimize the effects of external motion.

In a third step ("displacement calculation"), a displacement calculation may be performed on the filtered and down sampled data produced by the preprocessor. The algorithm may use the compression rate calculated by the ROSC algorithm to isolate a segment of data corresponding to a period of time approximately 10% greater than the compression interval and containing all range bins over that interval. This segment may be processed with a cross-correlation operation to identify the maximum shift of the static return pattern generated by the internal organs in the chest due to the compressions. The range bin shift may be converted to a displacement in centimeters using the average dielectric of the chest and the width of the range bins. This process can be repeated continuously and two or more results can be averaged to smooth out the feedback to the rescuer, minimizing over-compensation by the rescuer. Enhancements to the displacement algorithm could allow calculation of additional compression-related metrics, such as relaxation time.

Figure 8:
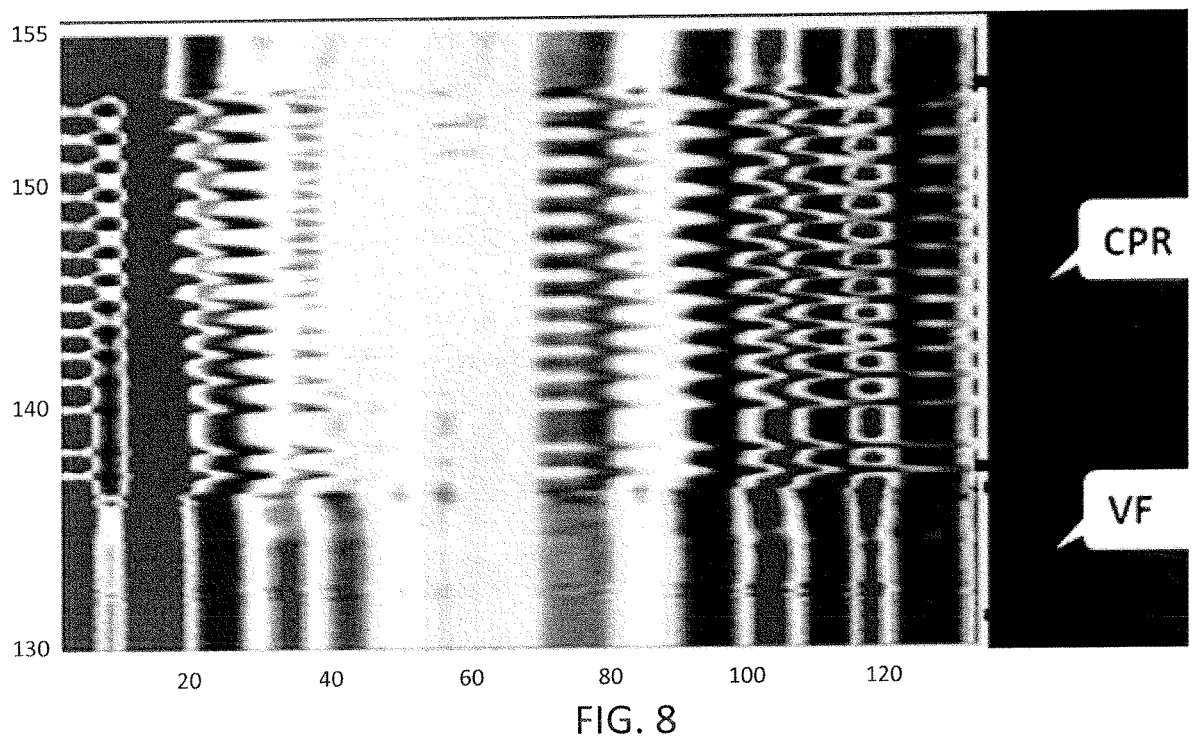
FIG. 8 is a graph (2D) showing compression data with a 1 cm mechanical displacement for chest compressions determined using a device such as the one shown in FIG. 1B.

FIG. 8 illustrates a 2-dimensional plot of the range bin data during mechanical compressions on a porcine model after ventricular fibrillation was induced. In the plot, the x-axis is increasing depth and the y-axis is increasing time. Several features from this example include: (1) there are a total of 14 compressions; (2) the first two compressions are followed by a short pause which in turn is followed by 12 compressions; and (3) the impact of the compressions is clearly visible through the range bins.

In this example, a mechanical thumper was set to a displacement of 1 cm and, using the radar data, the algorithm calculated a displacement of 1.08 cm, representing an error of 8%. This error is probably within acceptable limits and is most likely due to the limited timing resolution used in this series of experiments, slight inaccuracies in the dielectric model used in the calculations, and the fact that the deformation of organs by the compressions is not uniform throughout the chest. Further analysis and experiments should lead to lower errors.

FIGS. 10 and 11 illustrate variations of methods for determining compression rate (CR) and methods for determining compression strength (CS), respectively. The methods are very similar, as the resulting compression rate and/or compression strength may be used to inform the rescuer how to modify the CPR being applied while in real time.

Thus, ultra-wideband medical radar technology is capable of providing real-time, accurate information on the quality of chest compressions as well as the presence or absence of spontaneous circulation. This information may be critical for managing the application of CPR and cardiac resuscitation. The devices (including sensors) described herein and the associated algorithms, in combination with appropriate control and user interface software/hardware/firmware, can result in a small, rugged CPR guidance tool capable of providing timely feedback to the rescuer during the application of CPR.

In some variations, the devices could be designed as a low cost, stand-alone device appropriate for mass distribution to first responders (EMT, police, fire), schools, businesses, and participants in first aid/CPR courses. In addition, the technology could be embedded into gurneys, mechanical thumpers, vital signs monitoring equipment and defibrillators, including defibrillation patches/paddles. In laboratory tests of prototype devices similar to those described above, device operation was unaffected by cardio conversion shocks applied directly to the case of the device by an FDA approved and commercially available defibrillator.

When UWB is used as the energy and detection modality, the UWB antennas can be separated from the core circuitry by cables, allowing the antennas to be incorporated into a single-use patch or other medical fixtures, or they could be integrated into the devices. Internal memory could store the data from an entire resuscitation procedure to allow post-treatment review to improve training, device functioning, or any other evidentiary need. A wireless link may be used to allow real-time streaming of the data to a hospital for review by healthcare professionals, retrieval of the data after an event, as well as updates to the sensor firmware.

The devices described herein do not require direct contact of any conductive surfaces with the patient, allowing them to be completely encased in a fluid resistant case, enabling easy cleaning and minimizing the potential for contamination. If hermetically encased, the device's battery could be recharged using conductive contacts embedded into the case surface or via standard inductive charging circuitry. As optimal hand placement for CPR is on the sternum above the xiphoid, the case could be designed to take advantage of the shape of the xiphoid and nearby ribs and intercostal spaces to assist with placement of the sensor. It could also incorporate openings or manifolds to help caregivers place other medical devices or equipment. For example, a manifold port could be incorporated into the case to assist with placement and management of a sternal intraosseous infusion (IO) device.

Other sensor technologies could be incorporated with the UWB medical radar technology to provide additional medical data, improve accuracy, and/or reduce the potential for interference. For example, the addition of an accelerometer or gyroscope, both available in miniature, surface mount technology, could provide additional information on compressions as well as patient motion. Similarly, incorporation of ECG technology could provide information on the electrophysiology of the heart.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device for determining the return of spontaneous circulation (ROSC) when applying cardiopulmonary resuscitation (CPR), the device comprising:
    a surface configured to be placed against a patient's chest;
    an energy transmitter and energy receiver configured to emit energy from the surface into the patient;
    a processor coupled to the energy receiver and energy transmitter and configured to evaluate blood pressure from energy returning from the patient after being emitted into the patient, wherein evaluating the blood pressure includes: detecting one or more motion artifacts by combining multiple range bins and calculating a standard deviation of motion rates against a preset threshold value, calculating a baseline depth and computing a cardiac pulse strength and recalculating the baseline depth when the one or more motion artifacts are detected; and
    an output configured to indicate the ROSC based on the blood pressure evaluation of the processor.

2. The device of claim 1, further comprising a sealed housing including the surface.

3. The device of claim 1, wherein the energy transmitter and receiver comprise an ultra-wideband (UWB) transmitter and receiver configured to emit energy into a patient and to receive reflected energy.

4. The device of claim 1, wherein the transmitter and receiver comprise a single antenna.

5. The device of claim 1, wherein the transmitter and receiver comprise separate transmitting and receiving antennas.

6. The device of claim 1, wherein the processor is configured to evaluate blood pressure based on the time-of-flight of energy returning from the patient after being emitted into the patient.

7. The device of claim 1, wherein the processor evaluates blood pressure by determining an estimate of heart wall motion from the energy returning from the patient after being emitted into the patient and compares this estimate to a threshold correlated with a known blood pressure.

8. The device of claim 1, wherein the processor is configured to evaluate blood pressure by determining one or more regions showing cardiac activity based on the power spectral density of the regions and using these regions to evaluate blood pressure.

9. The device of claim 1, wherein the processor is further configured to determine CPR compression rate based on energy returning from the patient after being emitted into the patient.

10. The device of claim 1, wherein the processor is further configured to determine CPR compression depth based on energy returning from the patient after being emitted into the patient.

11. The device of claim 1, wherein the processor is configured to automatically evaluate blood pressure when compressions are not being applied.

12. The device of claim 1, wherein the output comprises a notification that that the patient has or has not returned to spontaneous circulation.

13. The device of claim 1, wherein the output comprises one or more of: a visual output, an audible output or a tactile output.

14. The device of claim 1, wherein the output comprises one or more visual indicators.

15. The device of claim 1, wherein the device is configured as a defibrillator.

16. The device of claim 1, wherein the device is configured as a mechanical compression device.

17. A device for determining the return of spontaneous circulation (ROSC) when applying cardiopulmonary resuscitation (CPR), the device comprising:
    a surface configured to be placed against a patient's chest;
    an energy transmitter and energy receiver configured to emit energy from the surface into the patient;
    a processor coupled to the energy receiver and energy transmitter and configured to evaluate blood pressure from energy returning from the patient after being emitted into the patient, wherein evaluating the blood pressure includes: detecting one or more motion artifacts by combining multiple range bins and calculating a standard deviation of motion rates against a preset threshold value, calculating a baseline depth and computing a cardiac pulse strength and recalculating the baseline depth when the one or more motion artifacts are detected; and an output configured to indicate the ROSC and to guide compression based on the processor's evaluation of energy returning from the patient after being emitted into the patient.

18. A device for determining the return of spontaneous circulation (ROSC) when applying cardiopulmonary resuscitation (CPR), the device comprising:

an ultra-wideband (UWB) transmitter and receiver configured to emit energy into a patient and to receive reflected energy;

a processor coupled to the UWB transmitter and receiver receiver and energy transmitter and configured to evaluate blood pressure based on the time-of-flight of the reflected energy returning from the patient, wherein evaluating the blood pressure includes:

detecting one or more motion artifacts by combining multiple range bins and calculating a standard deviation of motion rates against a preset threshold value, calculating a baseline depth and computing a cardiac pulse strength and recalculating the baseline depth when the one or more motion artifacts are detected; and an output configured to indicate the ROSC and to guide compression based on the processor's evaluation of the time-of-flight of the reflected energy.

19. A method of determining the return of spontaneous circulation (ROSC) when applying cardiopulmonary resuscitation (CPR), the method comprising:

placing a device against the patient's chest, wherein the device comprises an energy transmitter and energy receiver configured to emit energy from the surface into the patient and a processor coupled to the energy receiver and energy transmitter;

performing CPR on the patient;

emitting energy from the device into the patient's chest;

detecting energy reflected from the patient's chest;

evaluating the patient's blood pressure from the energy reflected from the patient's chest, wherein evaluating the blood pressure includes: detecting one or more motion artifacts by combining multiple range bins and calculating a standard deviation of motion rates against a preset threshold value, calculating a baseline depth and computing a cardiac pulse strength and recalculating the baseline depth when the one or more motion artifacts are detected; and indicating based on the evaluated blood pressure if the patient has returned to spontaneous circulation.

20. The method of claim 19, wherein placing the device comprises placing the device on the patient's chest before initiating CPR.

21. The method of claim 19, wherein emitting energy from the device comprises emitting ultra-wideband radio frequency energy into the patient.

22. The method of claim 19, wherein detecting energy reflected from the patient's chest comprises sampling a different times to determine values at different depths into the body.

23. The method of claim 19, wherein evaluating the patient's blood pressure comprises determining time-of-flight of the reflected energy.

24. The method of claim 19, wherein evaluating the patient's blood pressure from the energy reflected from the patient's chest comprises estimating when compressions are not being applied.

25. The method of claim 19, wherein evaluating the patient's blood pressure from the energy reflected from the patient's chest comprises determining an estimate of heart wall motion from the reflected energy and comparing the estimate of pulse strength to a threshold correlated with a known blood pressure.

26. The method of claim 19, wherein evaluating the patient's blood pressure from the energy reflected from the patient's chest comprises evaluating blood pressure by determining one or more regions showing cardiac activity based on the power spectral density of the regions and using these regions to evaluate blood pressure.

27. The method of claim 19, further comprising determining CPR compression rate based on the reflected energy, and outputting an indicator of compression rate.

28. The device of claim 19, further comprising determining CPR compression depth based on the reflected energy, and outputting an indicator of compression depth.

* * * * *